(12) United States Patent
Monier

(10) Patent No.: US 8,313,339 B2
(45) Date of Patent: Nov. 20, 2012

(54) CONNECTION DEVICE AND MEDICAL SYSTEM FOR ACQUIRING ELECTRIC SIGNALS PROVIDED WITH SUCH A CONNECTION DEVICE

(75) Inventor: Hubert Monier, Conflans-Sainte-Honorine (FR)

(73) Assignee: Integral Process, Conflans-Sainte-Honorine (FR)

( * ) Notice: Subject to any disclaimer, the term of this patent is extended or adjusted under 35 U.S.C. 154(b) by 174 days.

(21) Appl. No.: 12/747,216

(22) PCT Filed: Dec. 9, 2008

(86) PCT No.: PCT/FR2008/001713
§ 371 (c)(1),
(2), (4) Date: Aug. 26, 2010

(87) PCT Pub. No.: WO2009/103873
PCT Pub. Date: Aug. 27, 2009

(65) Prior Publication Data
US 2010/0312135 A1    Dec. 9, 2010

(30) Foreign Application Priority Data
Dec. 10, 2007  (FR) .................................... 07 08574

(51) Int. Cl.
*H01R 4/24* (2006.01)
(52) U.S. Cl. ........................ 439/417; 439/908
(58) Field of Classification Search .......... 439/404–417, 439/908
See application file for complete search history.

(56) References Cited

U.S. PATENT DOCUMENTS

| | | | |
|---|---|---|---|
| 5,147,215 A | 9/1992 | Pritulsky | |
| 5,622,168 A | 4/1997 | Keusch et al. | |
| 5,890,924 A * | 4/1999 | Endo et al. | 439/417 |
| 5,997,361 A * | 12/1999 | Driscoll et al. | 439/701 |
| 6,283,768 B1 * | 9/2001 | Van Naarden | 439/76.1 |
| 6,338,655 B1 * | 1/2002 | Masse et al. | 439/638 |
| 6,786,775 B1 | 9/2004 | Hanrahan et al. | |
| 6,824,412 B2 * | 11/2004 | Clement | 439/290 |
| 7,097,513 B2 * | 8/2006 | Bryan | 439/676 |
| 7,335,066 B2 * | 2/2008 | Carroll et al. | 439/676 |

FOREIGN PATENT DOCUMENTS

| | | |
|---|---|---|
| EP | 1195855 A | 4/2002 |
| FR | 1416048 A | 10/1965 |
| WO | 99/23729 A | 5/1999 |
| WO | 01/76019 A | 10/2001 |

OTHER PUBLICATIONS

International Search Report dated Sep. 4, 2009.

* cited by examiner

*Primary Examiner* — Truc Nguyen
(74) *Attorney, Agent, or Firm* — Harness, Dickey & Pierce, PLC

(57) ABSTRACT

The invention relates to connection means including a female connector (2) and a male connector (1).
The female connector (2) includes:
- a case (23) including walls (9b, 10b, 11b, 12b) delimiting a cavity for receiving (4) a male connector (1); and
- contact fingers (24) extending along at least one of said walls (10b, 11b) and intended to cooperate with the matching contacts (15) of the male connector (1);
- isolation partitions (27) made of a dielectric material protruding from the wall or walls (10b, 11b) towards the inside of the cavity (4) and positioned between the contact fingers (24).

The invention also relates to a male connector (1) intended to be introduced into the cavity of said female connector (2).
In addition, the invention also relates to a medical system of acquisition of electric signals provided with such a connection device.

22 Claims, 5 Drawing Sheets

CONNECTION DEVICE AND MEDICAL SYSTEM FOR ACQUIRING ELECTRIC SIGNALS PROVIDED WITH SUCH A CONNECTION DEVICE

The invention relates to the field of connectics for the transmission of electric signals.

More particularly, the invention relates to a female connector, a male connector, a connection device for the transmission of electric signals including such male and female connectors and a medical system of acquisition of electric signals provided with such a connection device.

In the prior art, many types of connectors are known. Among these, RJ connectors (Registered Jack connectors) are international standards used more particularly for fixed phone devices or in the field of computer networks.

RJ connectors are composed of a female connector and a male connector. The female connector includes a case delimiting a cavity for receiving a male connector and contacts intended to cooperate with the matching contacts of the male connector, extending along one of the walls of the cavity. The male connector includes a body made of a dielectric material including a housing provided with an opening for the passage of cables and insulation-displacement contact clamps inserted into notches formed on one of the outer faces of the body.

This type of connector is not expensive, it is easy to manufacture and may be easily connected to the cables transmitting electric signals.

However, the electric isolation between the contacts of such connectors is very limited. Thus, when electric signals have a high intensity, the risks of occurrence of an electric arc between two contacts of the connectors are high.

Then, these connectors cannot be used in some fields of application.

This is more particularly the case in the field of medical systems of acquisition of electric signals such as, for example, systems for making electrocardiograms which cannot use connectors of the RJ type.

As a matter of fact, in such an application, the connectors are connected to cables associated with monitoring electrodes ECG placed close to a patient's heart. Then, it is possible to obtain signals enabling to study cardiovascular pathologies. For some pathologies, a strong electric discharge, i.e. a defibrillation discharge, is urgently applied to the patient, close to the heart. Now, if the electric discharges are applied when the electrodes are placed on the skin close to the patient's heart, there is an important risk that an electric arc will form between the contacts of the connector if the latter are not sufficiently isolated electrically. The formation of an electric arc must be totally prohibited since such a phenomenon might damage the device of acquisition of electrocardiographic signals which would thus no longer enable to follow the cardiac evolutions; and create harmful electromagnetic interferences. In addition, this phenomenon absorbs a part of the energy from the electric discharge and thus reduces the efficiency of defibrillation from the patient.

Consequently, the connectors of the RJ type cannot be used for this type of application and connectors with pins are usually used, which include a male connector including a plurality of contact pins and a female connector including a plurality of pin receiving cells separated by a dielectric material. However, such connectors are rather expensive and complex to manufacture. In addition, the connection of the connectors to the cables is most often welded, which increases all the more the cost of implementation.

The invention aims at solving the problems of the prior art mentioned above while providing a connection device which is both simple, not expensive and has a correct electric isolation between the contacts.

For this purpose, the invention provides, according to a first aspect, a female connector for the transmission of electric signals including:
  a case, including walls delimiting a cavity for receiving a male connector;
  first contact fingers extending parallel to a first wall and intended to cooperate with the matching contacts of the male connector; and
  isolation partitions made of a dielectric material protruding from the first wall towards the inside of the cavity and positioned between the first contact fingers.

Thus, manufacturing a female connector is simple and not expensive and the electric isolation is significantly improved thanks to the isolation partitions.

Advantageously, the connector includes second contact fingers extending parallel to a second wall opposite the first wall, and isolation partitions made of a dielectric material protruding from the second wall towards the inside of the cavity and positioned between the second contact fingers. The contact fingers are thus distributed along at least two opposite walls. According to the invention, two walls are used for the positioning of the fingers, which makes it possible to increase the distances between the contact fingers and thus increase isolation.

Advantageously, the first and second contact fingers are positioned in staggered rows with respect to each other. Thus, the contact fingers are regularly distributed on either side of the body of the male connector.

The insulation partitions may more particularly be made of polyamide which is the material of a very good compromise between isolation characteristics and cost.

The contact fingers may be made of brass. The brass is both advantageous and mechanically strong for a large number of connections.

In one embodiment, the contact fingers have a cylindrical section.

Advantageously, at least one of the walls of the case is provided with at least one polarising slot. Thus, the risks of inappropriate use of the connector are reduced.

Advantageously, at least one of the walls is provided with abutting means making it possible to hold the male connector in the cavity.

According to a second aspect, the invention provides a male connector for the transmission of electric signals including:
  a body made of a dielectric material intended to be introduced into a female connector according to the first aspect of the invention, including contact fingers and insulation partitions, said body including:
  a housing provided with an opening for the passage of cables;
  outer faces intended to be positioned opposite walls delimiting the cavity of the female connector;
  slots formed on at least a first outer face provided with a lumen opening into said housing; and
  contact clamps inserted into said lumens including contact tracks, intended to cooperate with the contact fingers of the female connector and an insulation-displacement portion extending in the housing;
each slot has dimensions adapted for receiving a contact finger in one of the isolation partitions so as to build a separation between said notch and a neighbouring notch.

Similarly, the manufacturing of the connector is simple and the connection of the cables to the male connector is easy using contact insulation-displacement clamps. In addition, for each notch, the contact finger and the contact claw, respectively of the female and the male connectors are isolated from the other contacts by isolation partition of the female connector and the barrier delimiting the notch which form an isolating obstacle.

Advantageously, each notch has, between the lumen and one edge of said notch, a first space for receiving the contact finger or an isolation partition. In addition, each notch has, between the contact clamp and the plane of the first wall, a second space for receiving an isolation partition or a contact finger.

Advantageously, notches provided with lumens opening into the housing are formed on the second outer face opposite the first outer face; with contact clamps being inserted into said lumens. In addition, the contact clamps inserted into the lumens of the first outer face and those of the second outer face are positioned in staggered rows. Thus, the contacts are regularly distributed and the distance between these is increased.

Advantageously, the insulation-displacement portion is a W-shaped, extending in the longitudinal plane of the connector and both branches of which are intended to cut the cable sheath. As such, a contact clamp makes it possible to obtain a good quality for the connection.

According to a third aspect, the invention relates to a connection device of the transmission of electric signals including a female connector according to the first aspect of the invention and a male connector according to the second aspect of the invention.

Then, according to a fourth aspect, the invention provides a medical system for the acquisition of electric signals including:
- electrodes intended to be put in contact with the patient's body;
- a device for the connection with electric signals processing means;
- cables connected on the one hand to said electrodes and on the other hand to the connection device;
- the connection device is a connection device according to a third aspect of the invention.

Then, as manufacturing the connector is easy, a medical system according to the invention is not expensive to manufacture and may be disposable. Consequently, such a medical system makes it possible to reduce the risks of infectious diseases connected, to the use of this system and/or get rid of sterilisation operations.

In addition, such a system may be simultaneously used for a defibrillation shock.

Other objects and advantages of the invention will appear while reading the following description which is given while referring to the appended drawings.

Figure 1:
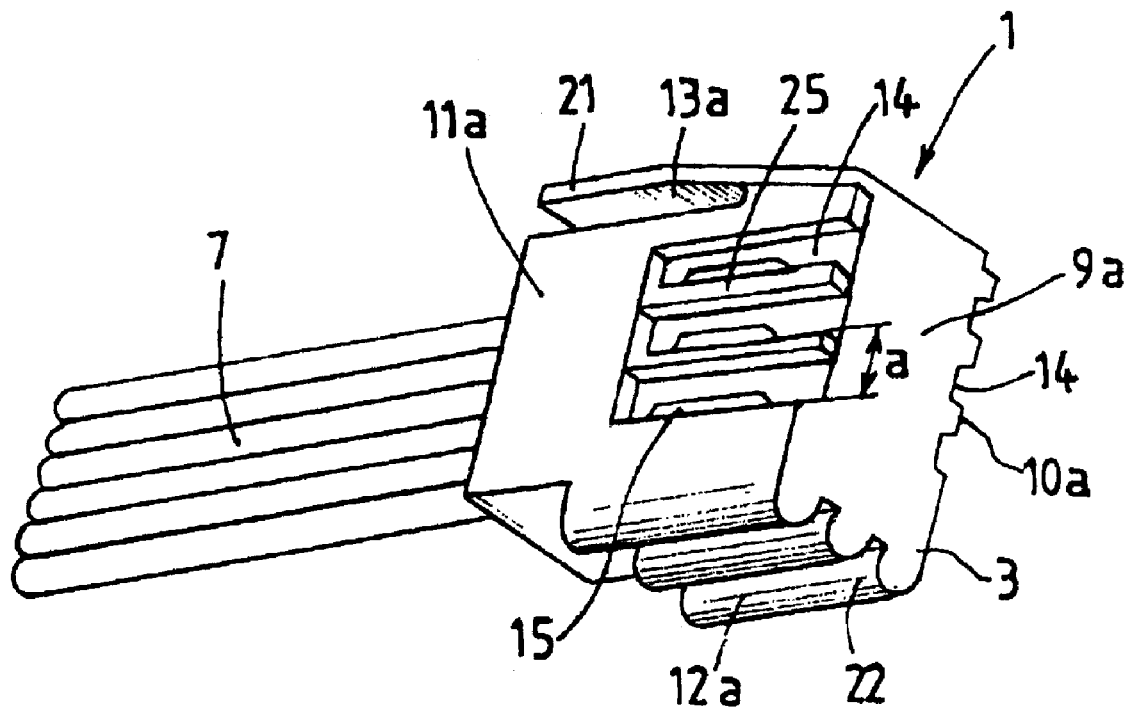
FIG. 1 is a perspective view of a male connector according to the invention.
Figure 2:
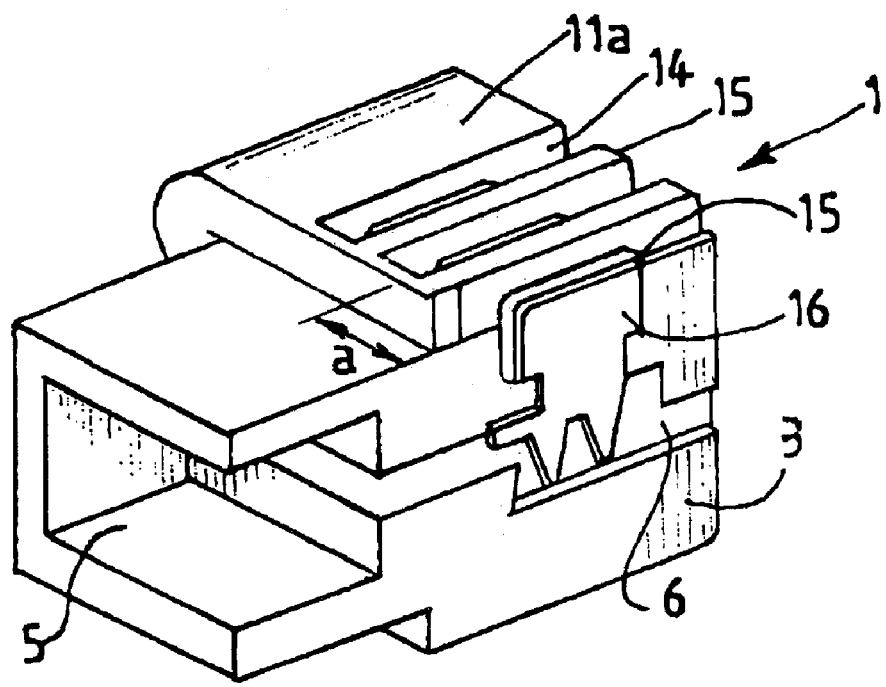
FIG. 2 is a perspective and cross-sectional view of the male connector of FIG. 1.
Figure 3:
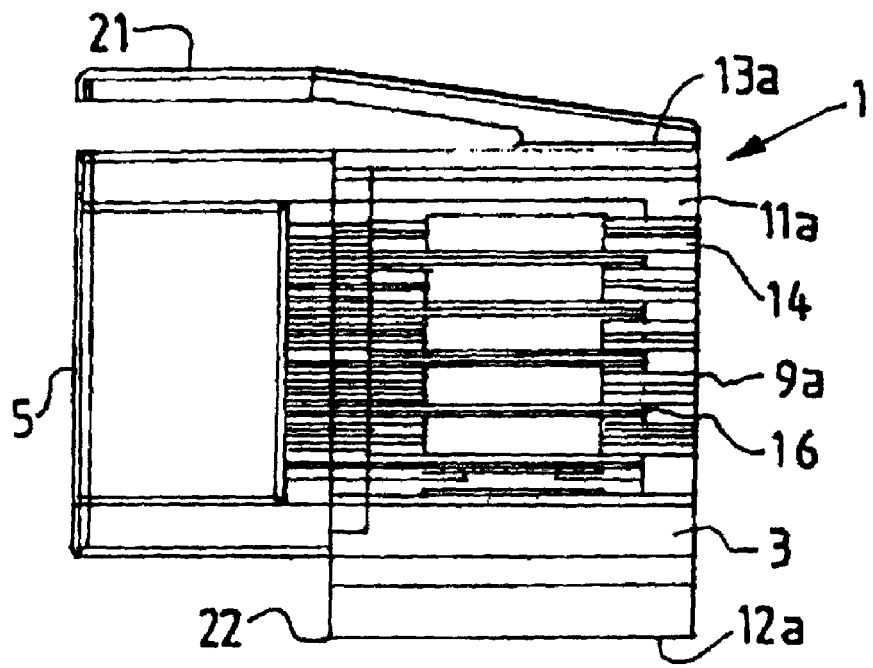
FIG. 3 is a top view of the male connector of FIG. 1.
Figure 4:
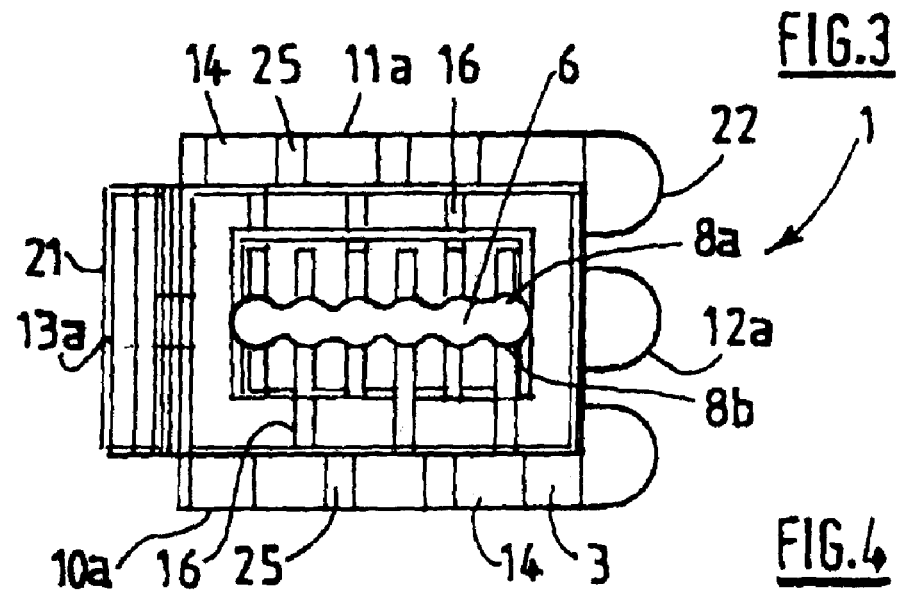
FIG. 4 is a rear view of the male connector of FIG. 1.

The male connector 1, illustrated in FIGS. 1 to 4, includes a body 3 made of a dielectric material intended to be introduced into the cavity 4 of the female connector 2. The body 3 is a part made of a moulded plastic and may more particularly be made of polycarbonate.

From the rear, the body 3 has an opening 5 opening into a housing 6 enabling the introduction of cables 7 inside said body 3. Advantageously, in order to guide the cables 7 inside the housing 6, the body 3 is provided with grooves 8a, 8b for guiding the cables 7 shown in details in FIG. 4. The grooves 8a, 8b are formed on the inner, upper and lower walls of the housing 6 and show a circle arc profile, the radius of which is slightly greater than the diameter of the cables 7.

The body 3 has five outer faces intended to come opposite the walls of the cavity of the female connector 2, a front face 9a, a right face 12a, a left face 13a, an upper face 11a and a lower face 10a.

Notches 14 for receiving contact clamps 15 are formed in the upper 11a and lower 10a faces of the body 3. The notches 14 are separated by isolation barriers 25 formed in said upper 11b and lower 10a faces. Advantageously, the notches 14 have a height of more than 0.8 mm, preferably more than or equal to 1 mm and a width of more than 1 mm, preferably more than or equal to 1.4 mm. In addition, the isolating barriers 25 have a thickness which is more than 0.5 mm, preferably more than or equal to 0.6 mm.

Lumens 16 opening inside the housing are formed in the notches 14. The lumens 16 enable the insertion of the contact clamps 15 inside the body 3.

Figure 5:
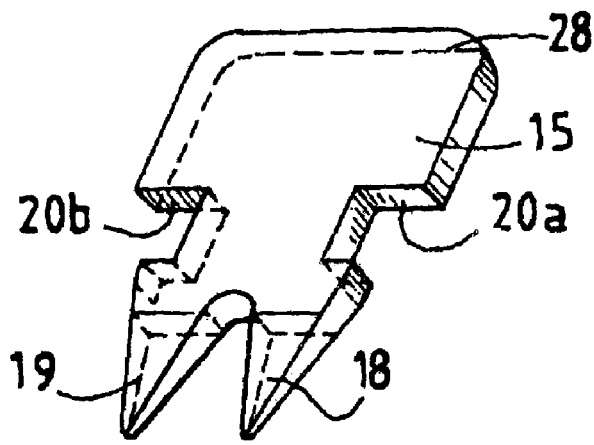
FIG. 5 shows a contact clamp of the male connector.

The contact clamps 15 shown in FIG. 5 include a contact track 28 which comes out of the case 3 and an insulation-displacement portion 17 inserted inside the housing 6. The insulation-displacement portion 16 is W-shaped, which extends in the longitudinal plane of the connector 1. Thus, both branches 18, 19 of the W cut the cable sheath 7 at two points spaced along each cable 7. The branches 18, 19 provide the electric connection and further make it possible to hold the cables 7 in the body 3. The contact claws 15 have two shoulders 20a, 20b abutting against two resting surfaces formed inside the lumens 16. In one embodiment, the contact clamps 15 may be made in a conductive x-ray transparent material, such as carbon, whereas in another embodiment, these are made of brass.

The contact clamps 15 as well as the notches 15 and the lumens 16 are positioned in staggered rows on either side of the body of the connector 1. The contact clamps 15 are positioned parallel to each other and are alternately oriented towards the upper face 11a and towards the lower face 10a. Then, the distances "a" separating the contact tracks, positioned on the same face 10a, 11a of the body 3 are increased, which makes it possible to increase the isolation between the contact clamps 15.

In addition, the insulation-displacement portions 17 of the clamps 15 alternately sink into the cables (7) from above and from under these. Then, the insulating-displacement portions 17 of two neighbouring clamps 15 are isolated by the isolation sheath of the cables 7. In addition, the cables 7 are held in grooves 8a, 8b, the dimensions of which are only slightly greater than those of the cables 7, and the body 3 also provides an electric isolation between the clamps 15 at the level of the housing 6.

The connection of cables 7 to the male connector 1 is carried out as follows. First, the cables 7 are inserted inside a housing 6 through the opening 5 and are abutted against the front inner wall of the housing 6. Then, the contact clamps 15 are pushed inside the housing 6 using crimping pliers for example, until the shoulders 20a, 20b abut against the resting surfaces formed in the lumens 16. Then, the branches 18, 19 are connected to the cables 7 while going through the isolation sheath. Consequently it is not necessary to strip the wires 7 before introducing same into the housing 6 of the male connector 1.

The connector 1 shown enables the connection of six cables. Then, in the embodiment shown, three notches 14 are formed in the upper face 11a and three notches 14, each one shifted laterally with respect to the notches 14 of the upper face 11a are formed in the lower face 10a.

In addition, the left side face 13a is provided with locking means including a resilient locking lug 21 and an abutting surface resting on the resilient lug 21. The abutting surface cooperates with the abutting means formed on the female connector so as to hold the male connector 1 in position in the cavity 4.

The right side face 12a is provided with a polarising slot 22, which is, in the embodiment shown, composed of three half-cylinders intended to be inserted into matching forms 29 provided in a wall 12b of the case 23 of the female connector 2.

Figures 7, 8:
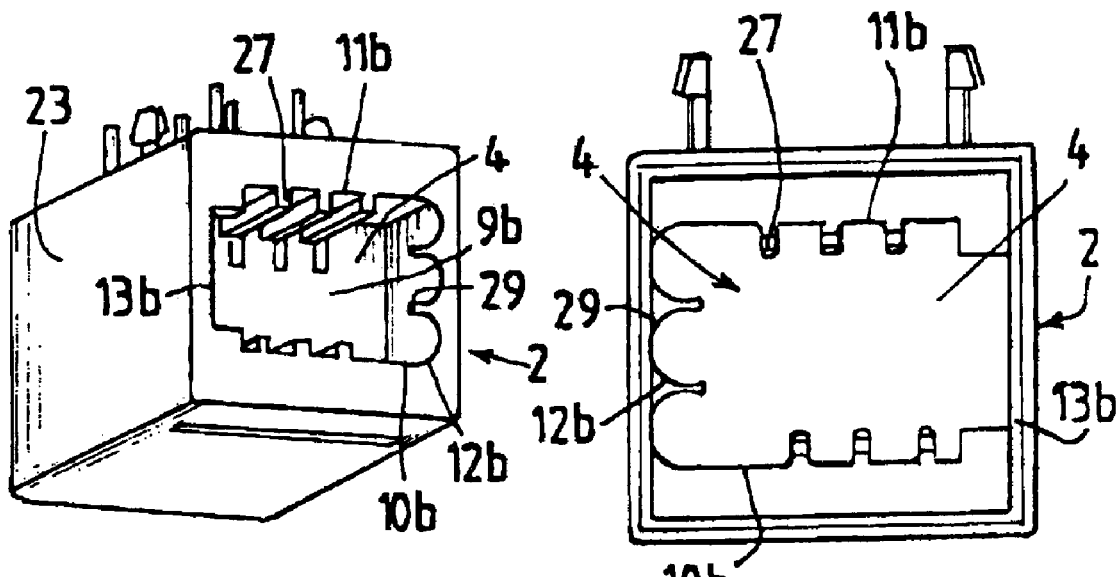
FIG. 7 is a perspective view of a female connector according to the invention.
FIG. 8 is a rear view of the case of the female connector of FIG. 7.

The female connector 2 illustrated in FIGS. 7 and 8, includes a case 23 provided with a cavity 4 delimited by five walls: a left 13b, a right 12b, an upper 11b, a lower 10b and a bottom wall 9b. The case 23 is also a piece of moulded plastic made of a dielectric material which may be particularly made out of polyamide.

Figure 9:
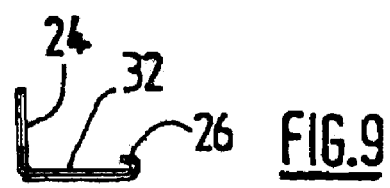
FIG. 9 is a side view of the contact finger of the female connector.

Contact fingers 24, illustrated in FIG. 9, include a contact portion 32 with extends along the upper 11b and lower 10b walls parallel to same. The contact portion 32 includes a curved end 26 coming into contact with the walls 10b and 11b and providing elasticity to the contact portion 32. In addition, the contact fingers 24 are preferably made of brass.

The positions of the contact fingers 24 on the upper 11b and lower 10b walls are so arranged that the tracks of said contact fingers 24 cooperate with the matching contact clamps 15 in the male connector 1. Then, the contact fingers 24 are also positioned in staggered rows. In the embodiment shown, the contact fingers 24 of the same wall 10b, 11b are separated by a distance of more than 1 mm, preferably more than or equal to 1.4 mm.

Isolation partitions 27 formed in the upper 11b and lower 10b walls are positioned between the contact fingers 24. The isolation partitions 27 protrude from the walls 11b, 10b towards the inside of the cavity 4. In the embodiment shown, the partitions 27 have a height of more than 0.8 mm preferably, of the order of 1 mm.

Figure 6:
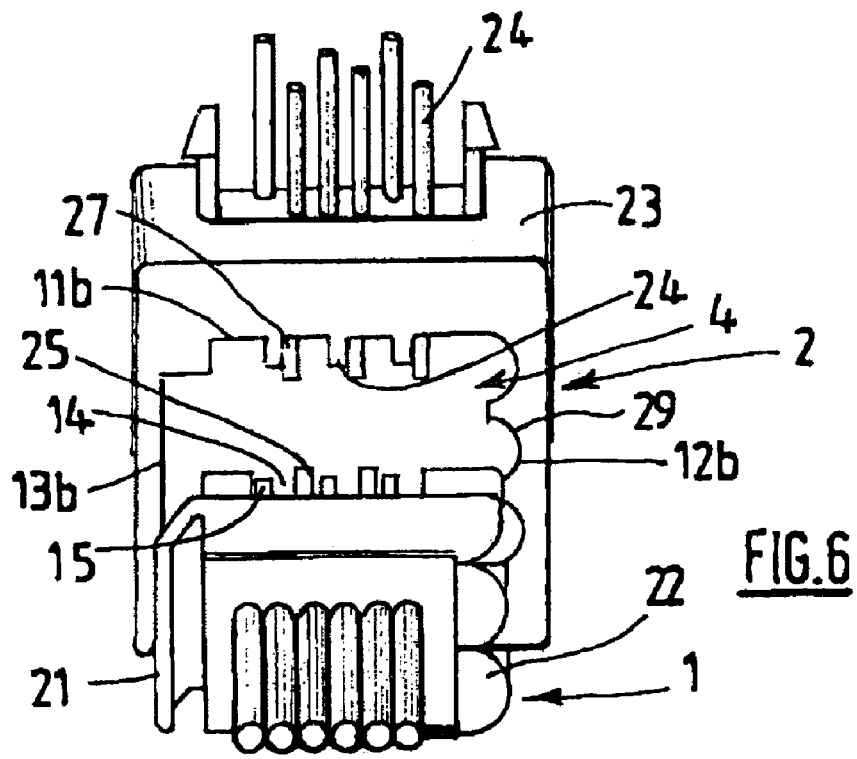
FIG. 6 is a perspective view illustrating the male connector and the female connector according to the invention, upon the introduction of the male connector into the female connector.
Figure 11:
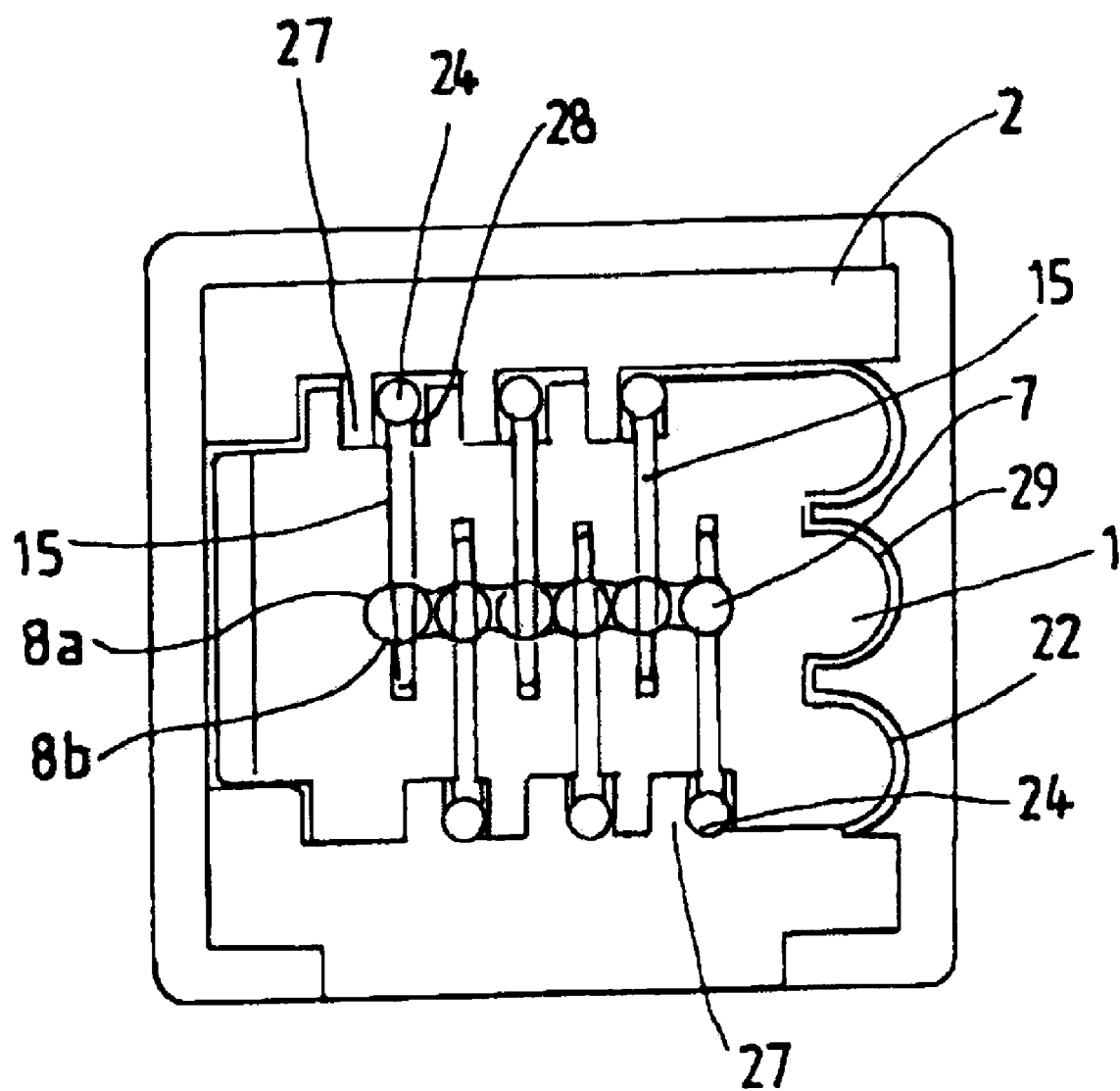
FIG. 11 is a detailed cross-sectional representation of a connection device according to the invention including a male connector inserted into the female connector.

As shown in FIGS. 6 and 11, the dimensions of the notches 14 of the male connector 1 are so arranged as to enable the insertion of a contact finger 24 and in isolation partition 27 inside said notch 14. As a matter of fact, when the male connector 1 is inserted into the cavity 4 of the female connector 2, the contact finger 24 cooperates with the contact clamp 15 so as to provide the connection and the isolation partition 27 builds a separation between said notch 14 and a neighbouring notch 14 together with the barrier 25.

In the embodiment shown in FIG. 11, the isolation partition 27 is received in a first receiving space 34 extending between the contact clamp 15 and one edge of the notch 14. The isolation partition 27 then cooperates with one edge of the notch 14 and builds, together with the barrier 25, an isolation partition with the neighbouring notch. In addition, the contact finger 24 comes into contact, in the opposite position, with the contact clamp 15 and is received in a second receiving space 35 extending between the contact clamp 15 and the plane of the wall 11a.

In another embodiment which is not shown, it may also be provided for the contact fingers 24 to have a cylindrical cross-section and to be received in a first receiving space 34 extending between the contact finger 15 and one edge of the notch 14. In this case, the contact between a finger 24 and a clamp 15 is a lateral one. In addition, the isolation partition 27 is received in the second receiving space 35 extending between the contact clamp 15 and the plane of the wall 11a.

It should also be noted that in the embodiment shown, one of the walls 12b of the case 23 is provided with at least one polarising slot 29 formed with three half-cylindrical cavities. In addition, the left wall 13b is provided with abutting means enabling to hold the male connector in the cavity.

In addition, the female connector 2 shown is intended to be connected to a printed circuit. For this purpose, a part of the contact fingers 24 comes out perpendicularly at the top of the case 23 as pikes, in order to enable the connection of the fingers to the tracks of the printed circuit. In addition, the case 23 is provided with fastening lugs 31 intended to be introduced into the holes provided in the printed circuits.

Figure 10:
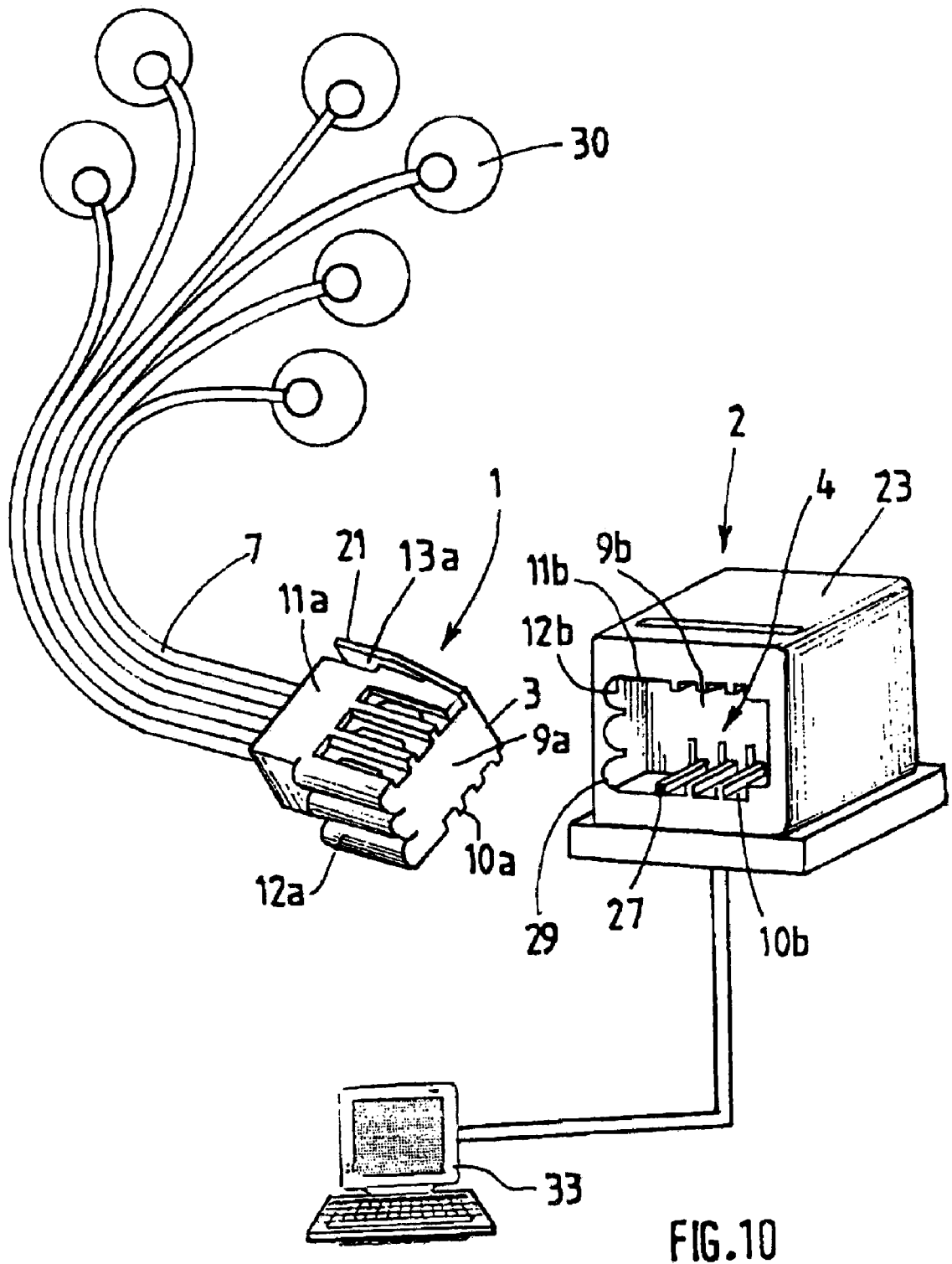
FIG. 10 is a schematic representation of the medical system of acquisition of electric signals from a human body according to the invention.

The medical system shown in FIG. 10 includes electrodes 30 which are intended to be positioned on a patient's body, a device for the connection to signal processing means 33 and cables 7. The connection device is composed of male 1 and female 2 connectors according to the invention. The cables 7 are connected on the one hand to an electrode 30 and on the other hand to a contact clamp 15 of the male connector 1.

In a preferred embodiment of the invention, the cables 7 used for the connection between the electrodes 30 and the main connector 1 are positioned in layers.

The invention is described above as an example. It should be noted that the persons skilled in the art may carry out various alternative embodiments of the invention without leaving the scope thereof.

It should also be noted that although the connectors shown are six-cable connectors, it is also possible to use, on the same principle, connectors for 4, 5, 7 or 8 cables or even more according to the desired configuration.

The invention claimed is:

1. A connection device for the transmission of electric signals including: a female connector including:
   a case including walls delimiting a cavity for receiving a male connector; and
   first contact fingers extending parallel to a first wall and intended to cooperate with matching contacts of the male connector;
   a male connector including:
   a body made of a dielectric material intended to be introduced into the female connector, said body including:
   a housing provided with an opening for the passage of cables;
   outer faces intended to be positioned opposite the walls delimiting the cavity of the female connector;
   notches formed on at least a first outer face provided with a lumen opening into said housing; and
   contact clamps inserted into said lumens including a contact track intended to cooperate with the contact fingers of the female connector and an insulation-displacement portion extending in the housing;

said connection device being characterised in that the female connector includes isolation partitions made of a dielectric material protruding from the first wall towards the inside of the cavity and positioned between the first contact fingers, and in that each notch of the male connector has dimensions adapted for receiving a contact finger and one of the isolation partitions so as to build a partition between said notch and a neighbouring notch.

2. A connection device according to claim 1, characterised in that the female connector includes second contact fingers extending parallel to a second wall opposite the first wall and isolation partitions made of a dielectric material protruding from the second wall towards the inside of the cavity and positioned between the second contact fingers.

3. A connection device according to claim 2, characterised in that the first and second contact fingers are positioned in staggered rows with respect to each other.

4. A connection device according to claim 3, characterised in that the contact fingers are separated by a distance of more than 1 mm, preferably equal to or greater than 1.4 mm.

5. A connection device according to claim 1, characterised in that the isolation partitions are made of polyamide.

6. A connection device according to claim 3, characterised in that the contact fingers are made of brass.

7. A connection device according to claim 3, characterised in that the contact fingers have a cylindrical cross-section.

8. A connection device according to claim 1, characterised in that at least one of the walls of the case is provided with at least one polarising slot.

9. A connection device according to claim 1, characterised in that at least one of the walls is provided with abutting means making it possible to hold the male connector in the cavity.

10. A connection device according to claim 1, characterised in that each notch has, between the lumen and an edge of said notch, a first space for receiving an isolation partition.

11. A connection device according to claim 1, characterised in that each notch has, between the contact clamp and the plane of the first wall, a second space for receiving a contact finger.

12. A connection device according to claim 1, characterised in that notches have a depth of more than 0.8 mm.

13. A connection device according to claim 1, characterised in that the notches have a width of more than 1 mm, preferably more than 1.4 mm.

14. A connection device according to claim 1, characterised in that notches provided with lumens opening into the housing are formed on the second outer face, opposite the first outer face with contact clamps being inserted into said lumens.

15. A connection device according to claim 14, characterised in that the contact clamps inserted into the lumens of the first outer face and those of the second outer face are positioned in staggered rows.

16. A connection device according to claim 1, characterised in that the contact tracks of the same outer face are separated by a distance of more than 1 mm, preferably more than or equal to 1.4 mm.

17. A connection device according to claim 1, characterised in that the body is made of polycarbonate.

18. A connection device according to claim 1, characterised in that the contact clamps may be made of carbon.

19. A connection device according to claim 1, characterised in that the insulation-displacement portion is W-shaped extending in the longitudinal plane of the connector and both branches of which are intended to cut the sheath of the cable.

20. A connection device according to claim 1, characterised in that at least one of the outer faces of the body is provided with at least one polarising slot.

21. A connection device according to claim 1, characterised in that at least one of the outer faces is provided with locking means including a resilient lug and an abutting surface intended to cooperate with an abutting surface of a female connector.

22. A medical system of acquisition of electric signals including:
- electrodes intended to be put in contact with a patient's body;
- a connection device with electric signals processing means;
- cables connected on the one hand to one of said electrodes and on the other hand to the connection device;
- said medical system being characterised in that the connection is a connection device according to claim 1.

* * * * *